United States Patent [19]
Newton et al.

[11] 4,152,219
[45] May 1, 1979

[54] SEPARATION OF ETHYLAMINES

[75] Inventors: Archie Newton; William Featherstone; Geoffrey K. Hobson, all of Middlesbrough, England

[73] Assignee: Imperial Chemical Industries Limited, London, England

[21] Appl. No.: 796,060

[22] Filed: May 11, 1977

[30] Foreign Application Priority Data

May 26, 1976 [GB] United Kingdom ............... 21820/76

[51] Int. Cl.$^2$ .............................................. B01D 3/16
[52] U.S. Cl. .................... 203/74; 260/585 B; 260/583 N
[58] Field of Search ...................... 203/74, 77, 81, 79, 203/83, 85, 91, 92, 96; 260/585 B, 583 N

[56] References Cited

U.S. PATENT DOCUMENTS

| | | | |
|---|---|---|---|
| 2,049,486 | 8/1936 | Babcock | 203/77 |
| 2,079,580 | 5/1937 | Swallen | 260/585 B |
| 2,998,357 | 8/1961 | Gillett et al. | 203/77 |

FOREIGN PATENT DOCUMENTS

421486 12/1934 United Kingdom ................ 260/585 B

OTHER PUBLICATIONS

Technical Week, Jul. 5, 1963, European Chemical News.

Primary Examiner—Hiram H. Bernstein
Attorney, Agent, or Firm—Cushman, Darby & Cushman

[57] ABSTRACT

Mono ethylamine and diethylamine are separated together by distillation from mixtures comprising mono-, di- and tri- ethylamine and water, and the mono ethylamine is separated from the diethylamine by a subsequent distillation.

9 Claims, 1 Drawing Figure

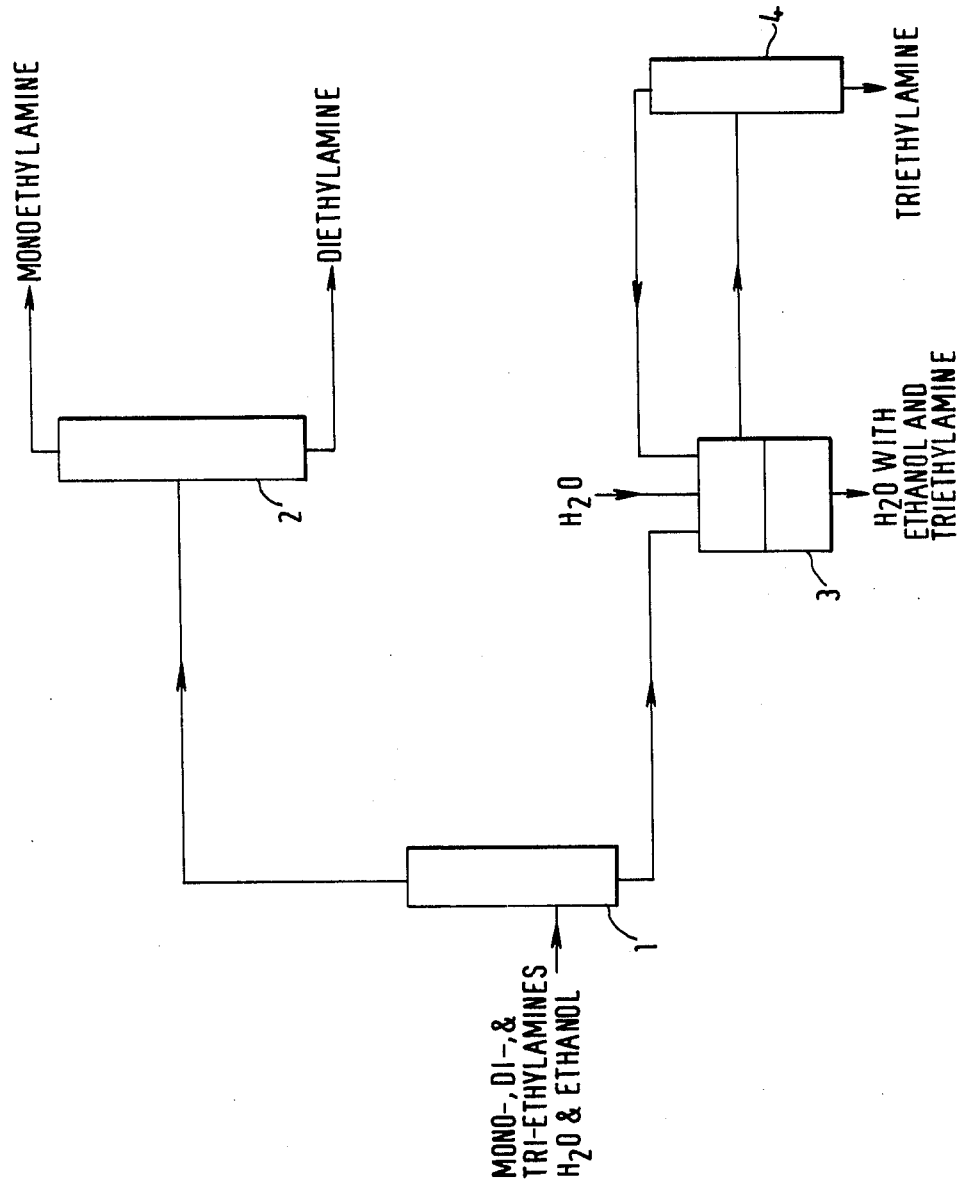

SEPARATION OF ETHYLAMINES

This invention relates to the separation of ethylamines.

In the manufacture of ethylamines by reacting ammonia with ethanol a mixture of mono- di and triethylamines with water and usually ethanol and ammonia may be obtained as a crude product. Ammonia may readily be removed from the product but the separation of other components by distillation presents some difficulty since diethylamine is difficult to separate from water.

We have found that diethylamine may readily be separated from water as a mixture with monoethylamine and that mono- and diethylamine may readily be separated by distillation from one another.

This invention comprises a process of treating mixtures comprising water, mono-, di- and triethylamine which comprises separating by distillation a mixture of mono- and diethylamine substantially free from water and triethylamine and separating by distillation monoethylamine from the said mixture of mono- and diethylamine.

If ethanol is present in the initial mixture it tends to remain with the triethylamine and water, which is separated as a bottoms product when the mixture of mono- and diethylamine is distilled from the mixture.

The distillation of the mixture of mono- and diethylamines from water and triethylamine may be carried out for example at a pressure of 0.1 to 1.5 bars and preferably at about atmospheric pressure and at a reflux ratio in the range 1:1 to 5:1 and preferably at about 2.5:1. Suitably the distillation column contains 20–80 and preferably 40–50 theoretical plates. The invention enables a wide range of compositions of mixtures comprising water, mono-, di- and triethylamines to be separated and the mixture of water and triethylamine and optionally ethanol may be treated by known means to recover triethylamine. If triethylamine is to be recovered from the mixture by phase separation for example after adding additional water, it is preferred that the diethylamine content of the mixture should be reduced to below 2.5% by weight.

The mixture of monoethylamine and diethylamine is preferably distilled at a pressure in the range 2–10 bars in order to avoid problems of condensation. A reflux ratio in the range 1:1 to 10:1 and preferably about 1.5:1 may be employed and the column may contain 15–60 and preferably 20–30 theoretical plates. Monoethylamine is recovered as a top product and diethylamine as a bottoms product.

It will be appreciated that the precise details of distillation techniques depend on the purity of product required.

Mixtures of water, triethylamine and optionally ethanol may be separated by adding water, decanting an upper layer comprising triethylamine together with some water and some ethanol if present and distilling that layer to give triethylamine as a bottoms product together with a top product, comprising water, triethylamine and ethanol if present which top product may be fed back to the decanter; and the bottom layer which is water rich but contains triethylamine and ethanol if present may be distilled to recover water as a bottoms product and triethylamine, ethanol and water as a top product which may be recycled.

EXAMPLE

A mixture comprising of 11% mono-ethylamine, 27.7% diethylamine, 15.7% triethylamine, 10% ethanol and 36.2% water by weight is fed at the tenth theoretical plate from the bottom to a distillation column 1 containing 40 theoretical plates which is operated on a reflux ratio of 2.5:1. The overheads from the column contain mono-ethylamine 29.5%, di-ethylamine 70.5%, water 0.03%, triethylamine 0.02% and less than 0.01% ethanol by weight. The bottoms from the column contain b 24.8% of triethylamine, 15.8% of ethanol, 2.2% of diethylamine and 57.2% of water and less than 0.01% of mono-ethylamine.

The overheads from the column are fed to the 15th theoretical plate from the bottom of a further column 2 having 27 theoretical plates which is operated at a reflux ratio of 1.5:1 at a pressure of 3 bars. The top product contains 99.9% of monoethylamine and the bottoms product contains 99.9% of diethylamine.

The bottoms product from the first column can be treated for the recovery of triethylamine by conventional means by adding water as shown at 3, separating the triethylamine rich layer and distilling from it in a still 4 a ternary azeotrope with ethanol and water and the binary azeotrope with water, triethylamine being recovered as a pure bottoms product. The overheads may be recycled to 3 for processing with incoming bottoms product from the first column.

We claim:

1. A process of separating a mixture comprising water, mono-, di and triethylamine which comprises separating from it by distillation a mixture of mono- and diethylamine substantially free from water and triethylamine and separating monoethylamine from the said mixture of mono- and diethylamine by distillation.

2. A process as claimed in claim 1 in which the first mixture comprises ethanol.

3. A process as claimed in claim 1 in which the distillation of mono- and diethylamines from water and diethylamine is carried out at a pressure of 0.1 to 1.5 bars and at a reflux ratio in the range 1:1 to 5:1.

4. A process as claimed in claim 1 in which the distillation of the mixture of mono- and diethylamines from water and triethylamine is carried out in a distillation column containing 20–80 theoretical plates.

5. A process as claimed in claim 1 in which triethylamine is separated from a mixture of water and triethylamine containing less than 2.5% by weight of diethylamine by adding water.

6. A process as claimed in claim 1 in which the mixture of monoethylamine and diethylamine is distilled at a pressure in the range 2–10 bars.

7. A process as claimed in claim 1 in which the mixtue of monoethylamine and diethylamine is distilled at a reflux ratio in the range 1:1 to 10:1 in a column containing 15–60 theoretical plates.

8. A process as claimed in claim 1 in which the mixture of water and triethylamine recovered from the first distillation is separated by adding water, decanting an upper layer comprising triethylamine together with water, and distilling that layer to give triethylamine as a bottoms product together with a top product comprising water and triethylamine, feeding the top product back to the decanter, distilling the bottom layer, recovering a top product comprising triethylamine and water and recycling the said top product to the decantation.

9. A process as claimed in claim 2 in which a mixture of water, triethylamine and ethanol recovered from the first distillation is separated by adding water, decanting an upper layer comprising triethylamine together with water and ethanol, and distilling that layer to give triethylamine as a bottoms product together with a top product comprising water, triethylamine and ethanol, feeding the top product back to the decanter, distilling the bottom layer, recovering a top product comprising triethylamine, water and ethanol and recycling the said top product to the decantation.

* * * * *